US006376493B1

(12) United States Patent
Jonas et al.

(10) Patent No.: US 6,376,493 B1
(45) Date of Patent: Apr. 23, 2002

(54) BENZOYLPYRIDAZINES

(75) Inventors: Rochus Jonas; Michael Wolf; Franz-Werner Kluxen, all of Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 09/830,957

(22) PCT Filed: Oct. 23, 1999

(86) PCT No.: PCT/EP99/08047

§ 371 Date: May 3, 2001

§ 102(e) Date: May 3, 2001

(87) PCT Pub. No.: WO00/26201

PCT Pub. Date: May 11, 2000

(30) Foreign Application Priority Data

Nov. 4, 1998 (DE) .......................... 198 50 701

(51) Int. Cl.⁷ ............... A61K 31/50; A61K 31/501; C07D 273/04; C07D 401/12
(52) U.S. Cl. .................. 514/252.03; 514/252.05; 514/247; 544/224; 544/238
(58) Field of Search ................. 544/224, 238; 514/252.03, 252.05, 247

(56) References Cited

FOREIGN PATENT DOCUMENTS

| EP | 738715 | * | 10/1996 |
| EP | 0738715 | | 10/1996 |
| WO | 9401412 | | 1/1994 |
| WO | 94/01412 | * | 1/1994 |
| WO | 98 06704 | | 2/1998 |
| WO | 98/06704 | * | 2/1998 |

OTHER PUBLICATIONS

Combs et al., *J. Med. Chem.* 38, p. 4878–4879, 1995.*
Combs DW: "Nonsteroidal Progesterone Receptor Ligands . . ." *Journal of Medicinal Chemistry*, American Chemical Society, vol. 38, No. 25 pp. 4878–4879, 1995.

* cited by examiner

*Primary Examiner*—Richard L. Raymond
(74) *Attorney, Agent, or Firm*—Millen, White, Zelano & Branigan, P.C.

(57) ABSTRACT

A group of compounds of, the preparation of, and the methods of use of benzoylpyridazine derivatives and the physiologically acceptable salts and solvates thereof, which have valuable pharmacological properties while well tolerated. They selectively inhibit phosphodiesterase IV with an intracellular increase in the CAMP level, and have an inhibitory effect on the formation of tumor necrosis factor.

11 Claims, No Drawings

BENZOYLPYRIDAZINES

This application a 371 of PCT/EP99/08047, filed Oct. 23, 1999.

The invention relates to benzoylpyridazine derivatives of the formula I

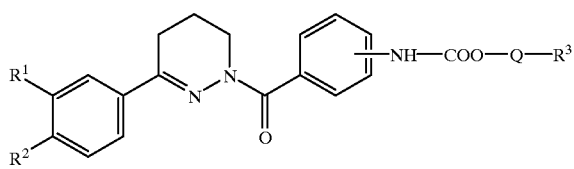

in which
- $R^1$, $R^2$ in each case independently of one another are —OH, $OR^5$, —S—$R^5$, —SO—$R^5$, —$SO_2$—$R^5$ or Hal, $R^1$ and $R^2$ together are also —O—$CH_2$—O—,
- $R^3$ is $NH_2$, NHA, NAA' or a saturated heterocycle having 1 to 4 N, O and/or S atoms which can be unsubstituted or mono-, di- or tri-substituted by Hal, A and/or OA,
- Q is absent or is branched or unbranched alkylene having 1–10 C atoms,
- $R^5$ is A, cycloalkyl having 3–7 C atoms, alkylenecycloalkyl having 4–8 C atoms or alkenyl having 2–8 C atoms,
- A, A' in each case independently of one another are alkyl which has 1 to 10 C atoms and which can be substituted by 1 to 5 F and/or Cl atoms and
- Hal is F, Cl, Br or I, and the physiologically acceptable salts and solvates thereof.

1-Benzoyltetrahydropyridazines have been described as progesterone receptor ligands, for example in J. Med. Chem. 38, 4878 (1995). Other arylalkanoylpyridazines are disclosed, for example, in DE 196 32 549.

The invention was based on the object of finding novel compounds which have valuable properties, in particular those which can be used for the reparation of pharmaceuticals.

It has been found that the compounds of the formula I and salts thereof have highly valuable pharmacological properties and are well tolerated.

In particular, they selectively inhibit phosphodiesterase IV combined with an intracellular increase in the cAMP level (N. Sommer et al., Nature Medicine, 1, 244–248 (1995)). The inhibition of PDE IV can be detected, for example, as described by C. W. Davis in Biochim. biophys. Acta 797, 354–362 (1984).

The compounds according to the invention can be employed for treating asthmatic diseases. The antiasthmatic effect of PDE IV inhibitors has been described by, for example, T. J. Torphy et al., in Thorax, 46, 512–523 (1991) and can be determined, for example, by the method of T. Olsson, Acta allergologica 26, 438–447 (1971).

Since cAMP inhibits osteoclastic cells and stimulates osteogenic cells (S. Kasugai et al., M681 and K. Miyamoto, M682, in Abstract of the American Society for Bone and Mineral Research 18th annual meeting, 1996, the compounds according to the invention can be used for the treatment of osteoporosis.

Moreover, the compounds have an inhibitory effect on the formation of TNF (tumour necrosis factor) and are therefore suitable for the treatment of allergies and inflammatory diseases, autoimmune diseases and transplant rejection reactions.

They can be used for the treatment of dysmnesia, tumours, cachexia, atherosclerosis, rheumatoid arthritis, multiple sclerosis, morbus Crohn, atopic dermatitis, diabetes mellitus, ulcerative colitis and AIDS.

The effect of PDE IV inhibitors in the treatment of asthma, inflammatory diseases, diabetes mellitus, atopic dermatitis, psoriasis, AIDS, tumour growth or tumour metastases is described, for example, in EP 77 92 91.

The anti-inflammatory effect of the substances according to the invention and their activity for the treatment of, for example, autoimmune diseases, multiple sclerosis or rheumatoid arthritis can be determined following the methods of N. Sommer et al., Nature Medicine, 1, 244–248 (1995) or L. Sekut et al., Clin. Exp. Immunol., 100, 126–132 (1995).

The effect of PDE IV inhibitors in the treatment of tumours is described, for example, in WO 95 35 281, WO 95 17 399 or WO 96 00 215.

The compounds of the formula I can be employed as pharmaceutically active ingredients in human and veterinary medicine. Furthermore, they can be employed as intermediates for the preparation of other pharmaceutically active ingredients.

Accordingly, the invention relates to the compounds of the formula I and to a process for the preparation of compounds of the formula I according to claim 1 and salts thereof, characterized in that a compound of the formula II

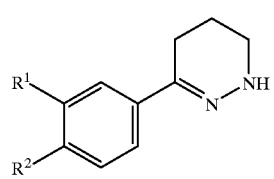

in which
$R^1$ and $R^2$ have the meanings given in claim 1 is reacted with a compound of the formula III

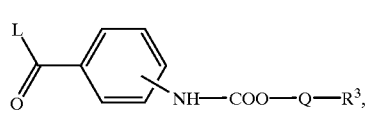

in which
Q and $R^3$ have the meanings given in claim 1 and is Cl, Br, OH or a reactive esterified OH group, or in that a compound of the formula IV

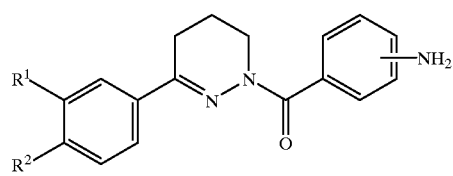

in which
$R^1$ and $R^2$ have the abovementioned meanings is reacted with a compound of the formula V

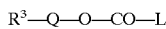

in which
$R^3$ and Q have the abovementioned meanings and L is Cl, Br, OH or a reactive esterified OH group, and/or in that a basic compound of the formula I is converted into a salt thereof by treatment with an acid.

The radicals, $R^1$, $R^2$, $R^3$, Q and L hereinabove and hereinbelow have the meanings given for the formulae I, II, III, IV and V, unless expressly stated otherwise.

The compounds of the formula I can have a chiral centre and can therefore occur in several stereoisomeric forms. The formula I includes all these forms (for example R- and S-forms) and their mixtures (for example the R,S-forms). Solvates are to be understood as meaning, for example, the hydrates or alkoxides of the compounds of the formula I.

A and A' are by preference alkyl, further preferably alkyl which is substituted by 1 to 5 fluorine and/or chlorine atoms.

In the above formulae, alkyl is by preference unbranched and has 1, 2, 3, 4, 5, 6, 7, 8, 9 or 10 C atoms, by preference 1, 2, 3, 4 or 5 C atoms, and is by preference methyl, ethyl, trifluoromethyl, pentafluoro-ethyl or propyl, furthermore preferably isopropyl, butyl, isobutyl, sec-butyl or tert-butyl, but also n-pentyl, neo-pentyl or isopentyl.

Cycloalkyl has by preference 3–7 C atoms and is preferably cyclopropyl and cyclobutyl, furthermore preferably cyclopentyl or cyclohexyl, furthermore also cycloheptyl.

Alkylenecycloalkyl has by preference 4–8 C atoms and is preferably methylenecyclopropyl and methylenecyclobutyl, furthermore preferably methylene-cyclopentyl and methylenecyclohexyl, furthermore also methylenecycloheptyl.

Alkenyl is by preference vinyl, 1- or 2-propenyl, 1-butenyl, isobutenyl, sec-butenyl, and is furthermore preferably 1-pentenyl, isopentenyl or 1-hexenyl.

Alkylene is unbranched or branched and is preferably methylene, ethylene, furthermore preferably propylene, butylene, pentylene, hexylene, furthermore heptylene, octylene, nonylene or decylene.

Hal is by preference F, Cl or Br, but also I.

The radicals $R^1$ and $R^2$ can be identical or different and are in the 3- or 4-position of the phenyl ring. For example, they are independently of one another hydroxyl, —S—CH$_3$, —SO—CH$_3$, —SO$_2$CH$_3$, F, Cl, Br or I or together methylenedioxy. However, especially preferably they are in each case methoxy, ethoxy, propoxy, isoproproxy, cyclopentoxy, or else fluoro-, difluoro- or trifluoromethoxy, 1-fluoro-, 2-fluoro-, 1,2-difluoro-, 2,2-difluoro-, 1,2,2-trifluoro- or 2,2,2-trifluoro-ethoxy.

$R^1$ is very especially preferably methyl, ethyl or isopropyl. $R^2$ is very especially preferably methyl.

Q is by preference for example a bond, methylene, ethylene, propylene, butylene or pentylene.

A heterocycle is by preference for example piperidinyl, tetrahydrofuranyl or pyrrolidinyl.

The radical $R^3$ is by preference also amino, N-methylamino, N,N-dimethylamino, N-ethylamino, N,N-diethylamino or N-methylpiperidin-4-yl.

The rule that all radicals which occur more than once can be identical or different, that is to say are independent of one another, applies to the entire invention.

Accordingly, the invention relates in particular to those compounds of the formula I in which at least one of the abovementioned radicals has one of the preferred meanings given above. Some preferred groups of compounds can be expressed by the following subformulae Ia to Ie which correspond to the formula I and in which radicals which are not defined in greater detail have the meanings given for the formula I, but where

| in Ia, | $R^1$ and $R^2$ | are in each case independently of one another OA, |
|---|---|---|
| | Q | is alkylene having 1–6 C atoms and |
| | $R^3$ | is piperidinyl, pyrazinyl or pyrrolidinyl, unsubstituted or mono- or disubstituted by Hal or A; |
| in Ib, | $R^1$ and $R^2$ | are in each case independently of one another OA, |
| | Q | is absent or is alkylene having 1–6 C atoms and |
| | $R^3$ | is NH$_2$, NHA or NAA', piperidinyl or pyrrolidinyl, unsubstituted or mono- or disubstituted by Hal or A; |
| in Ic, | $R^1$ and $R^2$ | together are —O—CH$_2$—O—, |
| | Q | is absent or is alkylene having 1–6 C atoms and |
| | $R^3$ | is NH$_2$, NHA or NAA', piperidinyl or pyrrolidinyl, unsubstituted or mono- or disubstituted by Hal or A. |

Besides, the compounds of the formula I and also the starting materials for their preparation are prepared by methods known per se as they are described in the literature (for example in the standard publications such as Houben-Weyl, Methoden der organischen Chemie [Methods in organic chemistry], Georg-Thieme-Verlag, Stuttgart), under reaction conditions which are known and suitable for the abovementioned reactions. It is also possible to utilize variants which are known per se but are not mentioned in greater detail in the present text.

In the compounds of the formulae II and IV, $R^1$ and $R^2$ have the abovementioned meanings, in particular the abovementioned preferred meanings.

In the compounds of the formulae III and V, Q is by preference methylene or ethylene, furthermore preferably propylene or butylene.

$R^3$ in the compounds of the formulae III and V has the abovementioned preferred meanings, while L is Cl, Br, OH or a reactive esterified OH group.

If L is a reactive esterified OH group, it is by preference alkylsulfonyloxy having 1–6 C atoms (preferably methylsulfonyloxy) or arylsulfonyloxy having 6–10 C atoms (preferably phenyl- or p-tolyl-sulfonyloxy, furthermore also 2-naphthalene-sulfonyloxy).

If desired, the starting materials can also be formed in situ, so that they are not isolated from the reaction mixture but immediately reacted further to give the compounds of the formula I.

On the other hand, it is possible to carry out the reaction stepwise.

By preference, the compounds of the formula I can be obtained by reacting compounds of the formula II with compounds of the formula III.

Some of he starting materials of the formulae II and III are known. If they are not known, they can be prepared by methods known per se.

In detail, the reaction of the compounds of the formula II with the compounds of the formula III is carried out in the presence or absence of an inert solvent at temperatures between approximately −20 and approximately 150°, preferably between 20 and 100°.

Examples of suitable inert solvents are hydrocarbons such as hexane, petroleum ether, benzene, toluene or xylene; chlorinated hydrocarbons such as trichloroethylene, 1,2-dichloroethane, carbon tetra-chloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane;

glycol ethers such as ethylene glycol monomethyl ether, ethylene glycol monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, or mixtures of the abovementioned solvents.

Moreover, compounds of the formula I can be obtained by reacting compounds of the formula IV with compounds of the formula V. As a rule, the starting compounds of the formulae IV and V are known. If they are not known, they can be prepared by methods known per se.

Thus, for example, the preparation of 1-benzoyl-tetrahydropyridazine is described in J. Med. Chem. 38, 4878 (1995).

In the compounds of the formula V, the radical —CO—L is a pre-activated carboxylic acid, preferably a carboxylic acid halide.

The compounds of the formula IV are reacted with compounds of the formula V under the same conditions regarding reaction time, temperature and solvent as has been described for the reaction of the compounds of the formula II with compounds of the formula III.

A base of the formula I can be converted into the corresponding acid addition salt with an acid, for example by reacting equivalent amounts of the base and the acid in an inert solvent such as ethanol, followed by evaporation. Acids which are suitable for this reaction are, in particular, those which give physiologically acceptable salts. Thus, inorganic acids can be used, for example sulfuric acid, nitric acid, hydrohalic acids such as hydrochloric acid or hydrobromic acid, phosphorus acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfonic acid. Salts with acids which are physiologically not acceptable, for example picrates, can be used for isolating and/or purifying the compounds of the formula I.

On the other hand, the free bases of the formula I can be liberated from their salts using bases (for example sodium hydroxide, sodium carbonate, potassium hydroxide or potassium carbonate), if so desired.

The invention furthermore relates to the use of the compounds of the formula I and/or of the physiologically acceptable salts thereof for the preparation of pharmaceutical products, in particular via the non-chemical route. They can be brought into a suitable pharmaceutical form together with at least one solid, liquid and/or semi-liquid excipient or auxiliary and, if appropriate, in combination with one or more further active ingredients.

The invention also relates to pharmaceuticals of the formula I and to the physiologically acceptable salts thereof as phosphodiesterase IV inhibitors.

The invention furthermore relates to pharmaceutical products comprising at least one compound of the formula I and/or a physiologically acceptable salt thereof.

These products can be used as pharmaceuticals in human or veterinary medicine. Suitable excipients are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petroleum jelly. Pharmaceutical forms which are used for oral administration are, in particular, tablets, pills, sugar-coated tablets, capsules, powders, granules, syrups, liquids or drops; pharmaceutical forms which can be used, in particular, for rectal administration are suppositories; pharmaceutical forms which can be used for parenteral administration are, in particular, solutions, preferably oily or aqueous solutions, furthermore suspensions, emulsions or implants, and pharmaceutical forms which can be used for topical administration are, in particular, ointments, creams or powders. The novel compounds can also be lyophilized and the resulting lyophilizates used for example for the preparation of injectable products. The abovementioned products can be sterilized and/or comprise auxiliaries such as glidants, preservatives, stabilizers and/or wetting agents, emulsifiers, salts for modifying the osmotic pressure, buffer substances, colours, flavourings and/or one or more other active ingredients, for example one or more vitamins.

The compounds of the formula I and their physiologically acceptable salts can be employed for combating diseases where a raised cAMP (cyclo-adenosine monophosphate) level leads to the inhibition or prevention of inflammations and to muscular relaxation. The compounds according to the invention can be used especially in the treatment of allergies, asthma, chronic bronchitis, atopic dermatitis, psoriasis and other skin diseases and autoimmune diseases.

The substances according to the invention are generally preferably administered in doses of between approximately 1 and 500 mg, in particular between 5 and 100 mg, per unit dose. The daily dose is preferably between approximately 0.02 and 10 mg/kg body weight. However, the particular dose for each patient depends on a wide range of factors, for example on the efficacy of the specific compound employed, on the age, the body weight, the general state of health, the sex, the diet, the time and route of administration, the elimination rate, the drug combination and the severity of the respective disease to which the therapy is applied. Oral administration is preferred.

Compounds of the formula I may contain one or more asymmetric centres. In this case, they are usually present in racemic form. Racemates which have been obtained can be resolved mechanically or chemically by methods known per se to give their enantiomers. It is preferred to form diastereomers from the racemic mixture by reacting it with an optically active resolving agent.

Naturally, it is also possible to obtain optically active compounds of the formula I by the above-described methods by using starting materials which are already optically active themselves.

The formula I encompasses all stereoisomers and heir mixtures, for example the racemates.

All temperatures hereinabove and hereinbelow are given in ° C. In the examples which follow, "customary work-up" means: if required, water is added; if required, the pH is brought to between 2 and 10, depending on the constitution of the end product; the mixture is extracted with ethyl acetate or dichloromethane and separated; the organic phase is dried over sodium sulfate and evaporated; and the residue

| Mass spectrometry (MS): | EI (electron impact ionization) M⁺ |
|---|---|
| | FAB (fast atom bombardment) (M + H) ⁺ | is purified by chromatography on silica gel and/or by crystallization.

EXAMPLE 1

A solution of 1.40 g of 1-(4-aminobenzoyl)-3-(3-ethoxy-4-methoxyphenyl)-1,2,3,4-tetrahydropyridazine ("AB") in 80 ml of dichloromethane and 0.8 ml of pyridine is treated with 0.9 g of dimethylaminopropyl chloroformate in 15 ml of dichloromethane, and stirring is continued for 2 hours. Work-up is as usual, yielding 1.6 g of 3-dimethylaminopropyl (4-[3-(3-ethoxy-4-methoxyphenyl)-1,2,3,4-tetrahydropyridazine-1-ylcarbonyl]phenyl)-carbamate hemifumarate, m.p. 193°.

The following is obtained analogously by reaction of "AB"

with N-methylpiperidin-4-yl chloroformate: N-methylpiperidin-4-yl-{4-[3-(3-ethoxy-4-methoxyphenyl)-1,2,3,4-tetrahydropyridazin-1-ylcarbonyl]phenyl}-carbamate hydrochloride, m.p. 243°.

The following is obtained analogously by reaction of 1-(4-aminobenzoyl)-3-(3-isopropoxy-4-methoxyphenyl)-1,2,3,4-tetrahydropyridazine with dimethylaminopropyl chloroformate: 3-dimethylaminopropyl {4-[3-(3-isopropoxy-4-methoxyphenyl)-1,2,3,4-tetrahydropyridazin-1-ylcarbonyl]phenyl}-carbamate hydrochloride, m.p. 213°.

The following is obtained analogously by reaction of 1-(3-aminobenzoyl)-3-(3-ethoxy-4-methoxyphenyl)-1,2,3,4-tetrahydropyridazine with dimethylaminopropyl chloroformate: 3-dimethylaminopropyl {3-[3-(3-ethoxy-4-methoxyphenyl)-1,2,3,4-tetrahydropyridazin-1-ylcarbonyl]phenyl}carbamate fumarate, m.p. 181°.

EXAMPLE 2

The following compounds are obtained analogously to Example 1:

3-dimethylaminopropyl {3-[3-(3-cyclopentyloxy-4-methoxy-phenyl)-1,2,3,4-tetrahydropyridazin-1-ylcarbonyl]phenyl}-carbamate hydrochloride, m.p. 235°;
N-methylpiperidin-4-yl-{3-[3-(3-cyclopentyloxy-4-methoxy-phenyl)-1,2,3,4-tetrahydropyridazin-1-ylcarbonyl]phenyl}-carbamate;
3-dimethylaminopropyl {3-[3-(3-propyloxy-4-methoxy-phenyl)-1,2,3,4-tetrahydropyridazin-1-ylcarbonyl]phenyl}-carbamate hydrochloride, m.p. 189°;
3-dimethylaminopropyl {4-[3-(3,4-diethoxyphenyl)-1,2,3,4-tetrahydropyridazin-1-ylcarbonyl]phenyl}carbamate hydrochloride, mp. 175°;
N-methylpiperidin-4-yl {4-[3-(3,4-diethoxyphenyl)-1,2,3,4-tetrahydropyridazin-1-ylcarbonyl]phenyl}carbamate fumarate, m.p. 202°;
3-dimethylaminopropyl {3-[3-(3,4-dimethoxyphenyl)-1,2,3,4-tetrahydropyridazin-1-ylcarbonyl]phenyl}carbamate hydrochloride, m.p. 204°;
3-dimethylaminopropyl {4-[3-(3,4-dimethoxyphenyl)-1,2,3,4-tetrahydropyridazin-1-ylcarbonyl]phenyl}carbamate fumarate, m.p. 180°.

The examples which follow relate to pharmaceutical products:

Example A

Vials

A solution of 100 g of an active ingredient of the formula I and 5 g of disodium hydrogen phosphate in 3 l of twice-distilled water is brought to pH 6.5 with 2N hydrochloric acid, filter-sterilized, filled into vials, lyophilized under sterile conditions and sealed in sterile form. Each vial comprises 5 mg of active ingredient.

Example B

Suppositories

A mixture of 20 g of an active ingredient of the formula I is melted with 100 g of soya lecithin and 1400 g of cocoa butter, and the mixture is poured into moulds and left to cool. Each suppository comprises 20 mg of active ingredient.

Example C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of twice-distilled water. The pH is brought to 6.8, and the solution is made up to 1 l and sterilized by irradiation. This solution can be used in the form of eyedrops.

Example D

Ointment 500 mg of an active ingredient of the formula I are mixed with 99.5 g of petroleum jelly under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is tableted in the customary manner in such a way that each tablet comprises 10 mg of active ingredient.

Example F

Sugar-coated Tablets

A mixture is tableted analogously to Example E, and the tablets are subsequently coated in the customary manner with a coating of sucrose, potato starch, talc, tragacanth and colouring.

Example G

Capsules 2 kg of active ingredient of the formula I are filled into hard gelatin capsules in the customary manner so that each capsule comprises 20 mg of the active ingredient.

Example H

Ampoules

A solution of 1 kg of active ingredient of the formula I in 60 l of twice-distilled water is filter-sterilized, filled into ampoules, lyophilized under sterile conditions and sealed in sterile form. Each ampoule comprises 10 mg of active ingredient.

Example I

Spray for Inhalation 14 g of active ingredient of the formula I are dissolved in 10 l of isotonic NaCl solution, and the solution is filled into commercially available pump-operated spray containers. The solution can be sprayed into mouth or nose. One

What is claimed is:

1. A compound of formula I

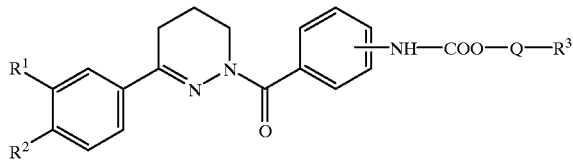

in which
R¹, R² in each case independently of one another are
—OH, OR⁵, —S—R⁵, —SO—R⁵, —SO₂—R⁵ or Hal,
or
R¹, and R² together are —O—CH₂—O—,
R³ is NH₂, NHA, NAA', piperidinyl, tetrahydrofuranyl or pyrrolidinyl each of which are unsubstituted or mono-, di-, or ti-substituted by Hal, A and/or OA,
Q is absent or is branched or unbranched alkylene having 1–10 C atoms,
R⁵ is A, cycloalkyl having 3–7 C atoms, alkylenecycloalkyl having 4–8 C atoms, or alkenyl having 2–8 C atoms,
A, A' in each case independently of one another are alkyl which has 1 to 10 C atoms and which is optionally substituted by 1 to 5 F and/or Cl atoms, and
Hal is F, Cl, Br or I,
or a physiologically acceptable salt or solvate thereof.

2. A compound of formula 1 of claim 1 wherein independently of each other, alkyl is methyl, ethyl, trifluoromethyl, pentafluorethyl, propyl, isopropyl, butyl, isobutyl, sec-butyl, tert-butyl, n-pentyl, neo-pentyl or isopentyl;
cycloalkyl is cyclopropyl, cyclobutyl, cyclopentyl, cyclohexyl or cycloheptyl;
alkylenecycloalkyl is methylenecyclopropyl, methylenecyclobutyl, methylenecyclopentyl, methylenecyclohexyl or methylenecycloheptyl;
alkenyl is vinyl, 1-propenyl, 2-propenyl, 1-butenyl, isobutenyl, sec-butenyl, 1-pentenyl, isopentenyl or 1 hexenyl; and
alkylene is methylene, ethylene, propylene, butylene, pentylene, hexylene, heptylene, octylene, nonylene or decylene.

3. A compound of formula I of claim 1 wherein R¹, R² in each case independently of one another are methoxy, ethoxy, propoxy, isopropoxy, cyclopentoxy, fluoromethoxy, difluoromethoxy, trifluoromethoxy, 1-fluoro-ethoxy, 2-fluoro-ethoxy, 1,2-difluoro-ethoxy, 2,2-difluoro-ethoxy, 1,2,2-trifluoro-ethoxy, or 2,2,2-trifluoro-ethoxy.

4. A compound of formula I of claim 1 wherein Q is methylene, ethylene, propylene, butylene or pentylene.

5. A compound of formula I of claim 1 wherein R³ is amino, N-methylamino, N,N-dimethylamino, N-ethylamino, N,N-diethylamino or N-methylpiperidin-4-yl.

6. A compound of formula I according to claim 1 which is selected from (a) 3-dimethylaminopropyl {4-[3-(3-ethoxy-4-methoxyphenyl)-1,2,3,4-tetrahydropyridazin-1-ylcarbonyl]-phenyl}carbamate;
(b) N-methylpiperidin-4-yl-{4-[3-(3-ethoxy-4-methoxypenyl)-1,2,3,4-tetrahydropyridazin-1-ylcarbonyl]-phenyl}carbamate;
(c) 3-dimethylaminopropyl {4-[3-(3-isopropoxxy-4-methoxy-phenyl)-1,2,3,4-tetrahydropyridazin-1-ylcarbonyl]-phenyl}carbamate; or
(d) 3-dimethylaminopropyl {3-[3-(3-ethoxy-4-methoxy-phenyl)-1,2,3,4-tetrahydropyridazin-1-ylcarbonyl]-phenyl}carbamate;

or a physiologically acceptable salt or solvate thereof.

7. A process for the preparation of a compound of formula I according to claim 1 or a salt thereof, which comprises:
reacting a compound of formula II

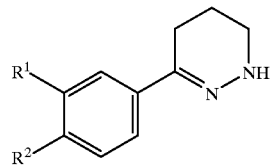

in which
R¹, and R² have the meanings given in claim 1 with a compound of formula III

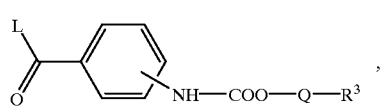

in which
Q and R³ have the meanings given in claim 1 and
L is Cl, Br, OH or a reactive esterified OH group; or reacting a compound of formula IV

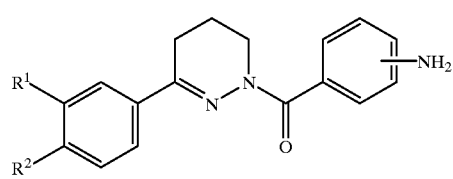

in which
R¹, and R² have the abovementioned meanings with a compound of formula V

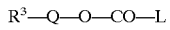   V in which
R³ and Q have the above-mentioned meanings and
L is Cl, Br, OH or a reactive esterified OH group; and/or converting a basic compound of formula I into a salt thereof by treatment with an acid.

8. A pharmaceutical product comprising at least one compound or formula I according to claim 1 and/or a physiologically acceptable salt thereof and at least one solid, liquid or semi-liquid excipient or auxiliary.

9. A process for the preparation of a pharmaceutical product, which comprises bringing a compound of formula I according to claim 1 and/or a physiologically acceptable salt thereof into a suitable pharmaceutical form together with at least one solid, liquid or semi-liquid excipient or auxiliary.

10. A method of treating a disease by inhibiting phosohodiesterase IV and/or the formation of tumor necrosis factor which comprises administering an affective amount of a compound of formula I of claim 1 and/or a physiologically acceptable salt thereof.

11. A method of treating osteoporosis, tumors, cachexia, atherosclerosis, rheumatoid arthritis, multiple sclerosis, diabetes mellitus, ulcerative colitis, inflammatory diseases, allergies, asthma, autoimmune diseases, AIDS or transplant rejection reactions which comprises administering a compound of formula I of claim 1 and/or a physiologically acceptable salt thereof.

* * * * *